United States Patent [19]

Lazarus et al.

[11] Patent Number: 4,529,694
[45] Date of Patent: Jul. 16, 1985

[54] CELL FUSION

[75] Inventors: Herbert Lazarus, Newton; Jerrold F. Schwaber, Brookline, both of Mass.

[73] Assignees: The Children's Medical Center Corporation, Boston; Dana-Farber Cancer Institute, Inc., Newton, both of Mass.

[21] Appl. No.: 369,141

[22] Filed: Apr. 16, 1982

[51] Int. Cl.³ ............ C12P 21/00; C12N 15/00; C12N 5/00; C12R 11/91
[52] U.S. Cl. .................. 435/68; 435/172.2; 435/240; 435/948; 424/85; 935/93; 935/100; 935/106
[58] Field of Search ........... 435/172, 240, 241, 948, 435/68; 424/85, 88; 935/93, 99, 100, 106, 108

[56] References Cited

FOREIGN PATENT DOCUMENTS 2079313  1/1982  United Kingdom ............... 435/240

OTHER PUBLICATIONS

Olsson et al, "Human Human Hybridomas Producing Monoclonal Antibodies of Predefined Antigenic Specificity", Proceedings of the National Academy of Sciences, 77(9), (1980), pp. 5429-5431.
Shulman et al, "A Better Cell Line for Making Hybridomas Secreting Specific Antibodies", Nature, 276, (11-1978), pp. 269-270.
Weiss, "Cell Hybridization: A Tool for the Study of Cell Differentiation", Somatic Cell Genetics by Caskey et al, (1982), pp. 169-182.
Levy et al, "Mouse-Human Hybridomas. The Conversion of Non-Secreting Human B Cells into Ig Secretors", Current Topics in Microbiology and Immunology, 81, (1978), pp. 170-172.
Galfre et al, "Chemical Typing of Human Kappa Light Chain Subtypes Expressed by Human Hybrid Myelomas", Immunology, 45, (1982), pp. 125-128.
Laskov et al, "Induction of IgM Secretion by Fusing Murine B-Lymphoma with Myeloma Cells", Current Topics in Microbiology and Immunology, 81, (1978), pp. 173-175.
Kamei et al., (1968), Experientia, 24, 410.
Krueger et al., (1974), J. Immunol., 112, 1415.
Steinitz et al., Nature, (London, 1977), 269, 420.
Schwaber et al., Nature, (London, 1973), 244, 444.
Kohler et al., Nature, (London, 1975), 256, 495.
Croce et al., Nature, (London, 1980), 288, 488.

Primary Examiner—Thomas G. Wiseman
Assistant Examiner—John Edward Tarcza

[57] ABSTRACT

Human hybridomas producing a preselected human monoclonal antibody are prepared by fusing human lymphocytes with a hybrid fusion partner. The hybrid fusion partner is the result of fusing human lymphocytes with human myeloma cells at least once wherein the resulting hybrid cell is capable of being a functional human fusion partner.

10 Claims, No Drawings

CELL FUSION

BACKGROUND OF THE INVENTION

The development of systems for the production of human monoclonal antibodies has been considerably slower than the development of murine systems. In 1964 the first reports of the ability to propagate human lymphoid cell lines appeared (Pulvertaft (1964) The Lancet i, 238, 1064). Shortly after that Kamei and Moor (Kamei et al. (1968) Experientia 24, 410) demonstrated the induction of antibody synthesis by one of these cell lines (P3J) following antigenic stimulation in vitro. Attempts to confirm their work were unsuccessful (Krueger et al. (1974) J. Immunol. 112, 1415). More recent attempts to first select for B lymphocytes based on specific antigen recognition followed by their 'immortalization' by EBV transformation has led to the establishment of B lymphoid cell lines which synthesize specific antibodies (Steinitz et al. Nature (London 1977) 269, 420). Fusion of mouse myeloma cells with human immunocytes resulted in the production of hybrids synthesizing human immunoglobulins (Schwaber et al. Nature (London 1973), 244, 444). Application of this method to mouse lymphocytes led to the development of mouse monoclonal antibodies (Kohler et al. Nature (London 1975) 256, 495). In contrast, human antibody production by mouse-human hybrids was unstable. To overcome this instability, a human B lymphoid cell line (Croce et al. Nature (London 1980) 288, 488) and a human myeloma cell line (Ollson et al. (1980) P.N.A.S. U.S.A. 77, 5429) have been utilized as fusing partners for human immunocytes. While all of these systems have been employed with some success none has been demonstrated to work reliably enough to be generally accepted. Fougere et al. P.N.A.S. U.S.A. (1972) 69, 330 and Davidson P.N.A.S. U.S.A. (1972) 69, 951 showed that expression of differentiated properties in hybrid cells may depend on gene dosage. This or an operationally similar phenomenon was successfully applied to the construction of a non-producing mouse myeloma cell line (Shulman et al. Nature (London 1978) 276, 269).

SUMMARY OF THE INVENTION

In general, the invention features, in one aspect, a new human myeloma analog cell (i.e., a hybrid cell, a portion of which is a human myeloma cell) which, although producing no antibody of its own, can be fused to a variety of specific antibody-producing mammalian lymphocytes to form hybrids capable of producing the specific antibody. The new analog cells grow well in culture (doubling time on the order of every 16-20 hours), exhibit high fusion efficiency (on the order of $10^{-4}$ hybrids per analog cell fused), and support the production of high antibody yields. A culture of the new cell line was deposited in the culture collection of the American Type Culture Collection in Rockville, Md. on Apr. 16, 1982, identified there as LSM 2.7, and assigned ATCC accession number HB 8121.

In another aspect the invention features a method of producing an antibody to a particular antigenic determinant, the method including the steps of obtaining a mammalian lymphoctye (preferably a spleen cell, and most preferably a human spleen cell) committed to producing the antibody, fusing the lymphocyte to the human myeloma analog cell of the invention to form a hybrid cell, culturing the hybrid cell in culture media, and recovering the antibody from the culture media.

The lymphocyte is normally obtained from a mammal which has been immunized with the particular antigenic determinant. If a human lymphocyte is used, the method has the advantage of producing a totally human monoclonal antibody.

In yet another aspect the invention features the production, from an incompetent human myeloma cell (i.e., a cell incapable of supporting the production of antibody when fused to a mammalian lymphocyte), of a competent human myeloma analog cell capable of supporting the production of antibody when fused to a mammalian lymphocyte while advantageously failing to produce antibody of its own. The method involves fusing an incompetent human myeloma cell to a human lymphocyte to form a hybrid cell, and then determining whether the hybrid cell is both competent and fails to produce its own antibody, and is thus the desired human myeloma analog cell. If the hybrid cell is incompetent, it is fused to an additional human lymphocyte to form a further hybrid cell and competence and failure to produce antibody are again determined. The latter two steps are repeated until a competent human myeloma analog cell is produced.

In another aspect the invention features a hybrid cell, capable of producing an antibody to a particular antigenic determinant, composed of a human myeloma analog cell of the invention fused to a mammalian lymphocyte committed to producing the desired antibody. As stated above, the hybrid cell is of particular value when the lymphocyte is of human origin.

In still another aspect the invention features a method of increasing, to a desired level, or restoring, the antibody production of a hybridoma cell which previously produced a desired antibody at a first level and which has either stopped producing the antibody or has begun producing the antibody at a second, lower level, the method including fusing the hybridoma cell to one or more irrelevant lymphocytes, i.e., lymphocytes which do not produce a specific desired antibody.

Other features and advantages of the invention will be apparent from the following description of the preferred embodiment thereof, and from the claims.

DESCRIPTION OF THE PREFERRED EMBODIMENT

Cells of the human myeloma cell line H. S. Sultan (CRL 1484) were obtained from the American Type Culture Collection in Rockville, Md. The cells were found to have a doubling time of 24 hours. They produced no detectable antibody. Hybridomas formed with these cells and human spleen cells also produced no detectable antibody; i.e., the cells were found to be incompetent.

Ethylmethane sulfonate (EMS) mutagenesis was carried out by exposing the cells to 100 µg/ml of EMS in RPMI 1640, pH 7, for 24 hours. The cells were then washed and plated in graded two-fold dilutions in medium containing 30 µg/ml of 6-thioguanine (6-TG), as described in Orkin et al. (1975) P.N.A.S. U.S.A. 72, 98. Only wells with single microscopic colonies after 5 days of culture were selected. Another group of cells were exposed to increasing concentrations of 8-azaguanine (8-AG) until solid resistance developed. All clones were tested for inability to grow in HAT selective medium, as described in Littlefield (1966) Exptl. Cell Research 41, 190.

Twenty-four fusions were then performed between the 6-TG or 8-AG resistant human myeloma mutants (designated LSM 1.1 and LSM 1.2 respectively) and human lymphocytes, either peripheral blood lymphocytes, purified B cells, or spleen cells, all of which were obtained from subjects who had not been immunized using any specific antigenic determinant against which it was desired to obtain antibody; i.e., the lymphocytes were "irrelevant."

Fusions were performed using a 46% v/v solution of polyethylene glycol 6000 (PEG) (Sigma, St. Louis, Mo.) in Hanks' Balanced Salt Solution (HBSS), pH 7.6. Cells to be fused were washed with HBSS, PEG was slowly added to the pelleted cells, incubated for 1 min., and then diluted slowly with HBSS. Fused cells were then washed and plated in HAT-containing medium to select hybrid cells. Culture conditions were as described in Schwaber et al. (1978) J. Clin. Invest. 62, 302, except that RPMI 1640 or Alpha MEM (lacking nucleosides) was used.

Each fusion represented $20 \times 10^6$ LSM cells and $50-200 \times 10^6$ lymphocytes, and was placed in four 96 well plates. All of these wells were screened for the presence, in the supernatants, of human antibody (Ig), by means of a solid phase radioimmunoassay (RIA) using 125I labelled antiserum specific for human Ig. Goat anti-human Ig (Cappell Laboratories, Cochranville, Pa.) was incubated in 96 well polystyrene plates (Dynatech, Alexandria, Va.) for 12 hrs., blocked with 1% bovine serum albumin for 2 hrs., washed 3 times with phosphate buffered saline (PBS), and then incubated with the test supernatants for 1 hr. The plates were then washed 3 times, and incubated with 125I labelled goat antiserum to human Ig for 1 hr., washed 10 times, and the individual wells cut out and counted in a gamma counter. Of the more than 9,000 independently derived supernatants screened, none were found to contain human Ig.

Three colonies were examined for cytoplasmic Ig-containing cells using immunofluorescence of cytocentrifuged cell preparations. Slides were air dried, fixed in freshly prepared ethanol-glacial acetic acid (19:1) at $-20°$ C. and washed 3 times with PBS. The cells were then stained with fluorescein isothiocyanate or tetramethyl rhodamine isothiocyanate conjugated Fab'2 fragments of affinity purified rabbit or goat antisera to human mu, gamma, or delta heavy chains and kappa or lambda light chains for 30 min. in a humidified chamber. Following 3 washes with PBS, the slides were mounted with PBS-glycerol (1:1) and examined with a Leitz Orthoplan microscope equipped for incident-light fluorescence. Two of the colonies examined were found to have detectable cytoplasmic Ig, in contrast to the original myeloma cells, none of which contained cytoplasmic Ig.

Eight of the hybrids derived from independent fusions of LSM 1.1 or 1.2 with irrelevant human spleen cells were reselected for resistance to 6-TG or 8-AG, without additional mutagenesis. They were then fused with irrelevant peripheral blood and splenic lymphocytes to test for competence; i.e., ability to support antibody production when fused to a lymphocyte. Human peripheral blood was collected in preservative free heparin and mononuclear cells were obtained by sedimentation over Ficoll-Hypaque.

Twelve out of 40 fusions resulted in Ig secreting hybrids. Because these fusions were not seeded at cloning densities, it cannot be said that every hybrid resulting from these 12 fusions produced Ig. However, 144 out of 192 wells contained readily detectable Ig.

It was observed that all twelve of the Ig-secreting fusions had been performed with 2 of the original 8 LSM-human lymphocyte myeloma analogs. The other six analogs fused well but the resulting hybrids did not secrete Ig. One (designated LSM 2.7) of the two successful analogs had an apparent higher efficiency of fusion (1 hybrid/$10^4$ analog cells) than the other. The LSM 2.7 analog cells were examined, as described above, for cytoplasmic antibody and were found to contain none.

Spleens were obtained from ten patients undergoing splenectomy for Hodgkin's disease staging. As part of a program to reduce post-splenectomy susceptibility to infection the patients were immunized, 1 to 11 days prior to surgery, with Pneumovax (Merck, Sharp and Dohme, West Point, Pa.). Spleen cells were freed from stromal tissue by teasing with sterile forceps.

Spleen cells from the immunized patients were fused with LSM 2.7 cells, as described above. All ten fusions yielded hybrids which produced human immunoglobulin. The fusions were also tested for specific pneumococcal polysaccharide antibody secretion using a solid phase enzyme linked immune assay (ELISA) as described in Gray (1979) J. Immunol. Meth. 28, 187. Pneumovax was dialyzed against 300 volumes of distilled water for 6 hrs. and stored at $-70°$ C. until used. To 0.1 ml Pneumovax (1.4 mg/ml) were added, sequentially, 0.5 ml NaOH (0.01M), 0.5 mg cyanuric chloride, 0.1 ml poly D-lysine (1 mg/ml) (MW 70,000, Sigma, St. Louis, Mo.). Incubation was carried out at 4° C. for 2 hrs. The ligand was then diluted 1:30 in distilled water and 100 μl aliquots were distributed in 96 well round bottom polyvinyl chloride plates (Immulon, Dynatech, Alexandria, Va.), incubated for 12 hrs, blocked with 5% fetal bovine serum in HBSS for 2 hrs and washed 3 times with 0.15M NaCl containing 0.05% Tween 20. Test supernatants were added to the wells and incubated for 1 hr., washed 3 times with NaCl-Tween, and then incubated with peroxidase conjugated goat anti-human Ig (Cappell Laboratories, Cochranville, Pa.) for 1 hr. The plates were washed 3 times with NaCl-Tween and 3 times with PBS after which substrate solution(O-phenylenediamine in 0.1M citrate buffer, pH 4.5) was added. Blocking experiments were done by preincubating 100 μl of test supernatants with 30 μl of dialyzed Pneumovax of identically prepared Meningovax AC or with each of the 14 individual pneumococcal capsular polysaccharides (generously provided by Dr. A. F. Woodhour, Merck, Sharp and Dohme, West Point, Pa.) for 1 hr prior to adding them to the wells.

Three of the ten fusions resulted in hybrid colonies which produced antibody which reacted with pneumococcal capsular polysaccharide but not with similarly prepared meningococcal antigen. Blocking experiments with each of the 14 pneumococcal polysaccharide subtypes were performed on supernatants obtained from one cloned population. Type 4 antigen alone inhibited reactivity of the positive supernatant for Pneumovax.

Analysis of the immunization history of the patients whose splenocytes were fused revealed that all three of the spleens which resulted in specific antibody producing hybrids came from patients who had been immunized either three or four days prior to surgery. None of the spleens derived from patients immunized at other intevals resulted in specific antibody production.

Repeated screening of hybrid cells revealed that antibody secretion regularly ceased between 28 and 42 days after fusion. Rigorous attempts to isolate Ig secreting cells by cloning and subcloning never resulted in isolation of a single clone with the capability for extended secretion of antibody. Whether maintained as mass cultures or by repeated cloning, the cessation of Ig secretion always occurred at the same time.

To determine whether these hybrid cells could be reactivated, a doubly cloned hybrid (LSM 2.7-A11) which had ceased antibody synthesis was fused to peripheral blood mononuclear cells of a normal donor. The hybrids were seeded in twelve wells each containing $1 \times 10E6$ LSM 2.7-A11 cells/well. All 12 wells contained hybrid colonies. When these were screened (10-20 days post-fusion), the supernatants of all 12 wells contained antibody specific for pneumococcal polysaccharide, indicating reactivation of the hybrids.

This reactivation by fusion with peripherol blood lymphocytes indicates that the cessation of antibody secretion is not due to loss of the structural genes coding for the antibody. Rather it must result either from loss of positive regulatory sites distant from the structural genes, or from intrinsic regulatory properties of the B lymphocytes.

In another experiment, LSM 2.7 cells were fused not to spleen cells of immunized patients, but to their peripheral blood lymphocytes. None of these fusions produced Pneumococcus-specific antibody, suggesting that, if there are peripheral blood cells capable of giving rise to antibody-producing hybrids, they are present only in very small numbers.

OTHER EMBODIMENTS

Other embodiments are within the following claims. For example, the LSM 2.7 myeloma analog line can be fused to other useful lymphocytes in addition to those producing antibody to Pneumococcus. The LSM 2.7 cells are most preferably fused to human lymphocytes, but can also be fused to other mammalian, e.g., mouse, lymphocytes.

The technique of producing competent human myeloma analogs from incompetent human myeloma cells by fusion to human lymphocytes is also broadly applicable. In some instances, only one fusion might be necessary, while in other cases more than two will be needed. Regardless of the number of fusions, the hybrids will be selected on the basis of competence and failure to produce their own antibody. When antibody production is detected after a fusion, this indicates that the hybrid used for that fusion is competent; if it also fails to produce antibody, it is a desirable analog.

The reactivation method of the invention is also broadly applicable, being useful for any hybridoma cell line which has ceased antibody production for reasons other than loss of structural genetic information. As with the analog-producing method, the number of fusions necessary can vary.

We claim:
1. A human myeloma analog cell from the strain deposited as ATCC HB 8121.
2. A method of producing an antibody to a particular antigenic determinant, said method comprising the steps of:
   (a) obtaining a mammalian lymphocyte capable of producing said antibody,
   (b) fusing said lymphocyte to a human myeloma analog cell from the strain deposited as ATCC HB 8121 to form a hybrid cell,
   (c) culturing said hybrid cell in culture media, and
   (d) recovering said antibody from said culture media.
3. The method of claim 2 wherein said lymphocyte is of human origin.
4. The method of claim 2 or claim 3 wherein said lymphocyte is a spleen cell.
5. The method of claim 2 wherein said lymphocyte capable of producing said antibody is taken from a mammal which has been immunized with said particular antigenic determinant.
6. A method of producing a competent human myeloma analog cell capable of supporting the production of antibody when fused to mammalian lymphocyte while failing to produce antibody of its own, said method comprising the steps of:
   (a) providing an incompetent human myeloma cell incapable of supporting the production of antibody when fused to a mammalian lymphocyte;
   (b) fusing said incompetent cell to a human lymphocyte to form a hybrid cell;
   (c) determining whether said hybrid cell is competent and fails to produce its own antibody and is thus said competent human myeloma analog cell;
   (d) if said hybrid fails to produce its own antibody but is incompetent, fusing said incompetent hybrid cell to an additional human lymphocyte to form a further hybrid cell, and determining whether said further hybrid cell is competent and fails to produce its own antibody and is thus said competent human myeloma analog cell; and
   (e) if said further hybrid cell fails to produce its own antibody but is incompetent, repeating said fusing and determining steps of (d) above until said competent human myeloma analog cell is produced.
7. The method of claim 6 wherein said fusing and determining steps of step (d) are repeated once.
8. A hybrid cell capable of producing an antibody to a particular antigenic determinant, said cell comprising a human myeloma analog cell from the strain deposited as ATCC HB 8121 fused to a mammalian lymphocyte capable of producing said antibody.
9. The hybrid cell of claim 8 wherein said mammalian lymphocyte is a human spleen cell.
10. The hybrid cell of claim 9 wherein said human spleen cell is committed to producing antibody specific to pneumococcal polysaccharide.

* * * * *